United States Patent
Yu et al.

(10) Patent No.: US 9,339,178 B2
(45) Date of Patent: May 17, 2016

(54) FORWARD SCANNING OPTICAL PROBES AND ASSOCIATED DEVICES, SYSTEMS, AND METHODS

(71) Applicant: Novartis AG, Basel (CH)

(72) Inventors: Lingfeng Yu, Lake Forest, CA (US); Kambiz Parto, Laguna Niguel, CA (US)

(73) Assignee: Novartis AG, Basel (CH)

( * ) Notice: Subject to any disclaimer, the term of this patent is extended or adjusted under 35 U.S.C. 154(b) by 161 days.

(21) Appl. No.: 14/139,326

(22) Filed: Dec. 23, 2013

(65) Prior Publication Data
US 2015/0173606 A1  Jun. 25, 2015

(51) Int. Cl.
*A61B 3/10* (2006.01)
*A61B 3/00* (2006.01)

(52) U.S. Cl.
CPC ............. *A61B 3/102* (2013.01); *A61B 3/0008* (2013.01)

(58) Field of Classification Search
CPC .... A61B 3/0008; A61B 3/102; A61B 3/1025; A61B 3/12; A61B 3/1208
USPC .................. 351/205, 206, 210, 221
See application file for complete search history.

(56) References Cited

U.S. PATENT DOCUMENTS

| | | | |
|---|---|---|---|
| 5,595,565 A | 1/1997 | Treat et al. | |
| 6,004,314 A | 12/1999 | Wei et al. | |
| 6,485,413 B1 * | 11/2002 | Boppart et al. | 600/160 |
| 7,261,687 B2 | 8/2007 | Yang | |
| 7,364,543 B2 | 4/2008 | Yang et al. | |
| 7,602,540 B2 | 10/2009 | Masuda et al. | |
| 8,325,988 B2 | 12/2012 | Ren et al. | |
| 2004/0254474 A1 | 12/2004 | Seibel et al. | |
| 2005/0020926 A1 | 1/2005 | Wiklof et al. | |
| 2005/0234345 A1 | 10/2005 | Yang | |
| 2006/0004397 A1 | 1/2006 | Osawa | |
| 2007/0066871 A1 | 3/2007 | Yang et al. | |
| 2007/0265602 A1 | 11/2007 | Mordaunt et al. | |
| 2008/0051770 A1 | 2/2008 | Scheller et al. | |
| 2009/0198125 A1 | 8/2009 | Nakabayashi et al. | |

(Continued)

FOREIGN PATENT DOCUMENTS

| | | |
|---|---|---|
| DE | 102008036420 | 11/2010 |
| GB | 2222953 | 3/1990 |

(Continued)

OTHER PUBLICATIONS

Han et al., "Handheld forward-imaging needle endoscope for ophthalmic optical coherence tomography inspection", Journal of Biomedical Optics, Mar./Apr. 2008, vol. 13(2), pp. 020505-1 thru 020505-3.

(Continued)

*Primary Examiner* — Huy K Mai
(74) *Attorney, Agent, or Firm* — Haynes & Boone, LLP

(57) ABSTRACT

Devices, systems, and methods that utilize a technique of changing a position of the set of optical fibers of the fiber bundle in cooperation with the scanning of the imaging light across a proximal surface of the fiber bundle to improve the resolution of the scanned image. In particular, a bundle actuator can be provided to change a position of the set of optical fibers of the fiber bundle in cooperation with a scanning of the imaging light across the proximal surface of the fiber bundle to cover the areas of the gaps between the optical fibers and to increase a resolution of the scanned image.

22 Claims, 6 Drawing Sheets

(56) References Cited

U.S. PATENT DOCUMENTS

| | | |
|---|---|---|
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0253949 A1 | 10/2010 | Adler et al. |
| 2011/0090486 A1 | 4/2011 | Udd |
| 2011/0184390 A1 | 7/2011 | Zanni et al. |
| 2011/0279821 A1 | 11/2011 | Brennan et al. |
| 2011/0282190 A1 | 11/2011 | Caffey et al. |
| 2011/0282191 A1 | 11/2011 | Brennan et al. |
| 2011/0282331 A1 | 11/2011 | Brennan et al. |
| 2012/0075639 A1 | 3/2012 | Brennan et al. |
| 2012/0190921 A1 | 7/2012 | Yadlowsky et al. |
| 2012/0245569 A1 | 9/2012 | Papac et al. |
| 2013/0038836 A1 | 2/2013 | Smith |
| 2013/0058533 A1 | 3/2013 | Ren et al. |
| 2013/0144278 A1 | 6/2013 | Papac et al. |
| 2013/0150839 A1 | 6/2013 | Smith et al. |
| 2013/0158392 A1 | 6/2013 | Papac et al. |
| 2013/0158393 A1 | 6/2013 | Papac et al. |
| 2013/0267776 A1 | 10/2013 | Brennan et al. |
| 2014/0327947 A1 | 11/2014 | Lin et al. |

FOREIGN PATENT DOCUMENTS

| | | |
|---|---|---|
| WO | 2007/038682 | 4/2007 |
| WO | 2008/079526 | 7/2008 |
| WO | 2012/100138 | 7/2012 |

OTHER PUBLICATIONS

Tearney GJ et al., "Scanning single-mode fiber optic catheter-endoscope for optical coherence tomography", Optics Letters, Apr. 1, 1996, vol. 21(7), pp. 543-545.

Wu et al., "Paired-angle-rotation scanning optical coherence tomography forward-imaging probe", Optics Letters, May 2006, vol. 31(9), 1265-1267.

Xie, T., "Fiber-optic-bundle-based optical coherence tomography", Opt. Lett. 30, 2005, pp. 1803-1805.

Yaqoob et al., "Methods and application areas of endoscopic optical coherence tomography", Journal of Biomedical Optics, Nov./Dec. 2006, vol. 11(6), pp. 063001-1 thru 063001-19.

International Search Report and Written Opinion issued for PCT/US2014/071188, dated Mar. 19, 2015, 8 pgs.

* cited by examiner

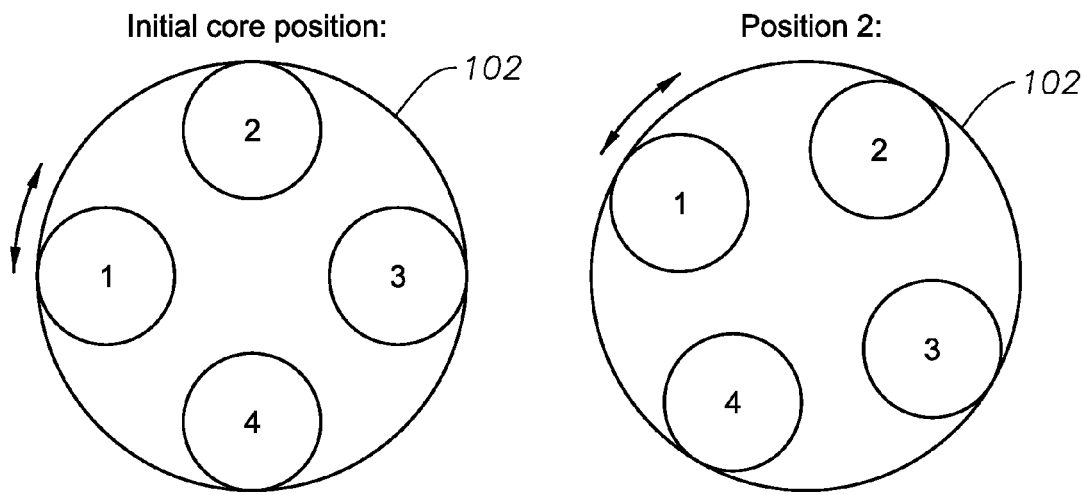
FIG. 2a
FIG. 2b
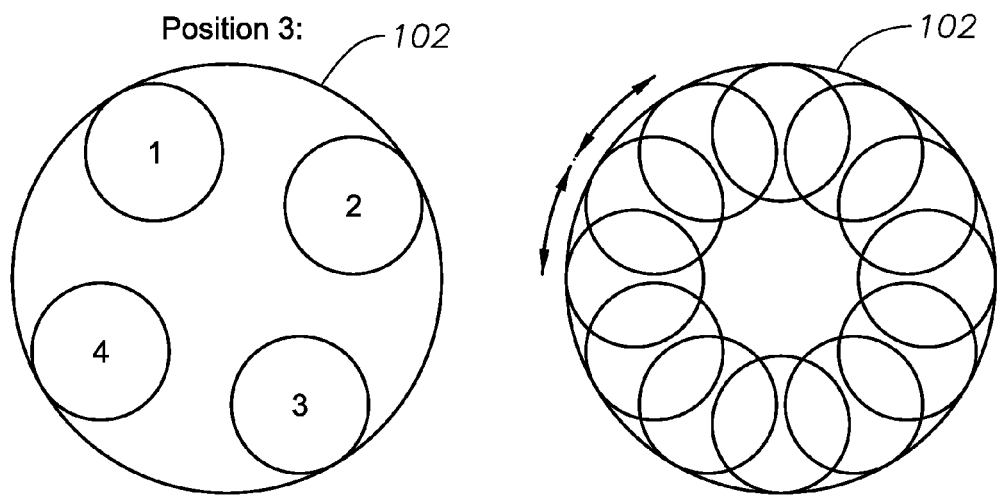
FIG. 2c
FIG. 2d

FORWARD SCANNING OPTICAL PROBES AND ASSOCIATED DEVICES, SYSTEMS, AND METHODS

TECHNICAL FIELD

Embodiments disclosed herein are related to devices, systems, and methods for scanning tissue with a forward scanning optical probe, and more particularly, to devices, systems, and methods that utilize an optical coherence tomography (OCT) probe, having a fiber bundle for ophthalmic imaging.

BACKGROUND

Optical Coherence Tomography (OCT) systems are used to capture and generate images of patient tissue layers. These systems often include OCT probes that can invasively penetrate tissue to obtain visualization of tissue within a patient. In ophthalmology, OCT probes are used to obtain detailed images of tissue about the eye or tissue forming a part of the eye, such as the retina.

The OCT probes often include a projecting cannula that can invasively penetrate patient tissue. The imaging probe scans tissue by refracting the optical light beam through a lens disposed at an end of the cannula. A scanner can steer an imaging light to scan the target tissues. The scanner can be placed at a distal end of the cannula of an OCT probe. Nevertheless, placing the scanner at the distal end of the cannula may cause the size of the distal end of the cannula to be bulky and have complex structure, which is not suitable for insertion into an eye.

As an alternative, the scanner can be placed outside the eye directly above the eye to be able to directly project the imaging light into the eye. Nevertheless, placing the scanner directly above the eye can interfere with an optical pathway of a surgical microscope and can take up essential operating space between the surgical microscope and the eye.

Accordingly, it is beneficial to position the scanner away from the optical pathway of the surgical microscope. For example, the scanner can be placed either in a handpiece of an OCT probe or in a separate scanning unit. If the scanner is placed away from the optical pathway, an optical guide is provided to guide the imaging light back to the cannula that is inserted inside the eye. The optical guide can be a fiber bundle formed by a bundle of optical fibers in order to have certain flexibility. Nevertheless, in a fiber bundle, there are finite gaps formed between the optical fibers. Thus, when an imaging light is scanned across a proximal surface of the fiber bundle, the scanning may be intermittently be interrupted when the imaging light passes through the gaps between the optical fibers. As a result, the output scanning beam can become jumpy, which can cause the scanning image to be grainy and noisy with insufficient resolution.

Accordingly, there is a need for devices, systems, and methods utilizing an OCT imaging system with a scanner scanning a fiber bundle that improve scanning resolution to be finer than a fiber-to-fiber separation of the fiber bundle and that address one or more of the needs discussed above.

SUMMARY

Embodiments disclosed herein are related to devices, systems, and methods that utilize an actuator that can adjust a position of optical fibers in a fiber bundle in cooperation with a scanner scanning an imaging light across a proximal surface of the fiber bundle to improve imaging resolution.

Consistent with some embodiments, an optical imaging apparatus is provided. The optical imaging apparatus can include a fiber bundle having a set of optical fibers configured to guide an imaging light, a beam forming unit configured to receive the imaging light from the fiber bundle and to redirect the imaging light to a target region, and a bundle actuator configured to adjust a position of the set of optical fibers of the fiber bundle. The optical imaging apparatus can include a scanning unit configured to scan the imaging light over a proximal surface of the fiber bundle to cause the redirected imaging light to scan along a scanning pattern in the target region.

The optical imaging apparatus also can include an imaging light source configured to generate the imaging light and a scanning unit configured to scan the imaging light over a proximal surface of the fiber bundle.

Consistent with some embodiments, a method of ophthalmic imaging is provided. The method can include scanning an imaging beam across a proximal end of a fiber bundle with a scanning unit; adjusting a configuration of a distal portion of the fiber bundle with a bundle actuator; and directing the imaging light by a beam forming unit to a target region.

Additional aspects, features, and advantages of the present disclosure will become apparent from the following detailed description.

BRIEF DESCRIPTION OF THE DRAWINGS

FIG. 2*a* illustrates a cross-sectional view of a fiber bundle.
FIG. 2*b* illustrates a cross-sectional view of a fiber bundle.
FIG. 2*c* illustrates a cross-sectional view of a fiber bundle.
FIG. 2*d* illustrates a cross-sectional view of a fiber bundle.

DETAILED DESCRIPTION

Figure 1:
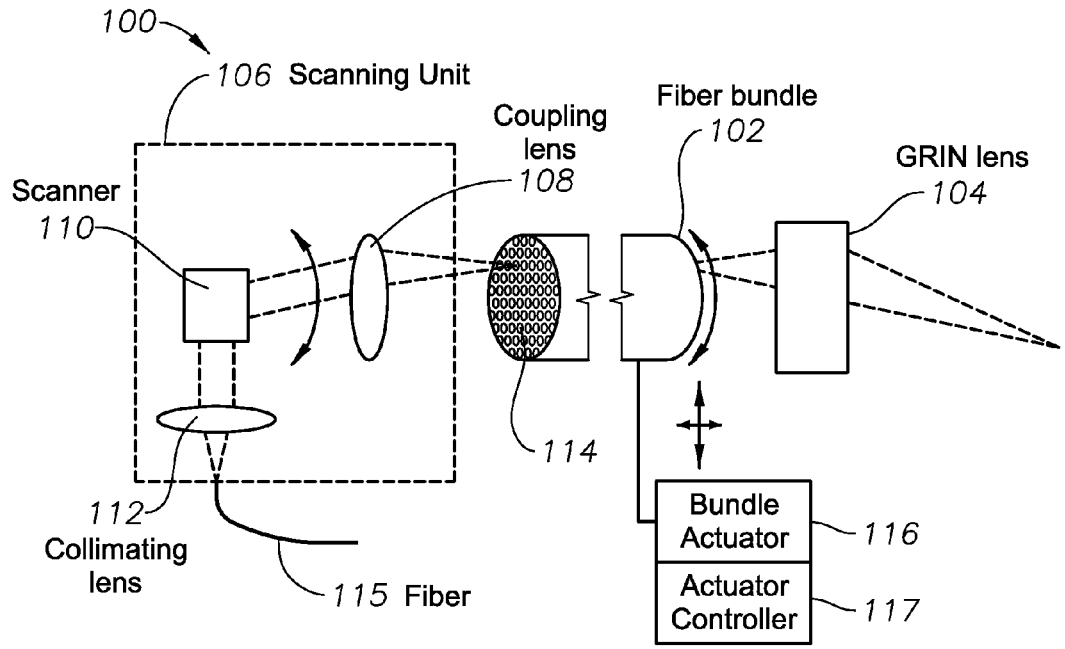
FIG. 1 illustrates an exemplary OCT imaging system.

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan an imaging light across a target tissue to generate an OCT image. The imaging probe can include a housing, or handle, and a cannula, protruding from the housing. The cannula can be configured to invasively penetrate patient tissue, such as the globe of an eye. The cannula can house a lens and a fiber bundle. The fiber bundle include a set of optical fibers each configured to direct an imaging light through the lens and capture reflected imaging light that passes back through the lens. A scanner can scan the imaging light across a proximal surface of the fiber bundle to obtain an image. Because there are inherent gaps between the individual optical fibers in the fiber bundle, the scanned image may become grainy or noisy.

Exemplary aspects described herein utilize a technique of changing a position of the set of optical fibers of the fiber bundle in cooperation with the scanning of the imaging light across a proximal surface of the fiber bundle to improve the resolution of the scanned image. In particular, a bundle actuator can be provided to change a position, or configuration, of the set of optical fibers of the fiber bundle in cooperation with a scanning of the imaging light across the proximal surface of the fiber bundle to cover the areas of the gaps between the optical fibers and to increase a resolution of the scanned image. Changing the position of the set of optical fibers can overcome one or more of the problems or limitations of previous approaches. As a result, embodiments of the present disclosure can (1) eliminate or reduce imaging artifacts associated with the spacing or separation between the individual optical fibers of a fiber bundle; (2) improve image clarity and/or resolution; and (3) increase the image sampling density.

FIG. 1 is a diagrammatic schematic view of an exemplary OCT imaging apparatus 100. In particular, the OCT imaging apparatus 100 can include a fiber bundle 102 and a beam forming unit 104. The fiber bundle 102 can include a set of optical fibers configured to guide an imaging light. The number of optical fibers in the fiber bundle 102 can vary in a wide range, including between 2 fibers to 10,000,000 fibers, 2 fibers to 1,000,000 fibers, 2 fibers to 100,000 fibers, and, 2 fibers to 10,000 fibers. Each optical fiber can have a size or diameter between 1 micron and 100 microns, between 2 microns and 50 microns, or between 5 microns and 20 microns. The individual fibers of the bundle can be single mode fibers, multi-mode fibers, single-mode waveguides, multi-mode waveguides, and hollow tubes.

The beam forming unit 104 can be configured to receive the imaging light from the fiber bundle 102 and to direct, or redirect, the imaging light to a target region. The beam forming unit 104 can focus the imaging light onto the target region. For example, the beam forming unit 104 can include a Gradient Index (GRIN) lens, a ball lens, a diffractive element, an aspherical lens, or an objective.

The OCT imaging apparatus 100 also can include a scanning unit 106 configured to scan the imaging light over/across a proximal surface 114 of the fiber bundle 102 to cause the redirected imaging light to scan along a scanning pattern in the target region. The scanning unit 106 can include a coupling lens 108, a scanner 110, and a collimating lens 112. An optical fiber 115 can guide the imaging light generated by an imaging light source to the scanning unit 106. The imaging light can be received by the collimating lens 112 from the optical fiber 115. The scanner 110 can receive the collimated imaging light from the collimating lens 112 and direct the imaging light to the coupling lens 108. The coupling lens 108 can couple the imaging light into a single or a few optical fibers of the fiber bundle 102.

The scanner 110 can include optical elements configured to scan the collimated beam of the imaging light. For example, the scanner 110 can include one or more of a rotatable mirror, a galvanometer, a resonant scanner, a polygon scanner, and a MEMS scanner. Thus, the scanner 110 can steer the direction of the imaging light to scan the imaging light across the proximal surface 114 of the fiber bundle 102. The scanning imaging light can be guided by the fiber bundle 102 toward the beam forming unit 104 and be directed or output by the beam forming unit 104 to scan the target region along a scanning pattern.

The OCT imaging apparatus 100 can include a bundle actuator 116 configured to actuate all or a portion of the fiber bundle 102. The bundle actuator 116 can be positioned adjacent to a proximal portion, a central portion, and/or a distal portion of the fiber bundle 102. In some implementations, the bundle actuator 116 can adjust a position, or configuration, of the set of optical fibers at the distal end of the fiber bundle 102. For example, the bundle actuator 116 can rotate, twist, laterally translate, and/or longitudinally translate the distal portion of the set of optical fibers of the fiber bundle 102.

The bundle actuator 116 can also be a portion of a manual- or auto-focus sub-system configured to longitudinally adjust the distal portion of the set of optical fibers of the fiber bundle 102 or the beam forming unit 104 to adjust a focal distance between the beam forming unit 104 and the target tissue. For example, the bundle actuator 116 can move the distal portion of the fiber bundle 102 toward or away from the beam forming unit 104 to adjust the focus of imaging beam. The bundle actuator 116 can include any number of components configured to facilitate rotating, twisting, laterally translating, and/or longitudinally translating the fiber bundle 102 or portion thereof. These components may include without limitation electric motor(s), bias element(s) (e.g., coil springs, leaf springs, etc.), mechanical interface(s) and/or connector(s) (e.g., pulleys, ramps, clamps, bolts, nuts, screws, nails, etc.), electromagnetic element(s) (e.g., permanent magnets, electromagnets, coils, etc.) pneumatic drivers, piezo-based drivers and/or combinations thereof.

FIGS. 2a-2d illustrate a cross-sectional view of the fiber bundle 102. FIG. 2a illustrates an embodiment in which the fiber bundle 102 has four optical fibers: core 1, core 2, core 3, and core 4. However, it is understood that the concepts described below are equally applicable to fiber bundles having any number of optical fibers, such as a number between 2 fibers and 10,000,000 fibers, 2 fibers and 1,000,000 fibers, 2 fibers and 100,000 fibers, and 2 fibers and 10,000 fibers.

In the four fibers, or four cores embodiment, the scanning unit 106 can scan the imaging light across the proximal surface 114, across the four cores 1-4. However, as described above, the imaging light emitted at the distal end of the fiber bundle 102 sequentially by the fibers 1-4 will hit four target or scanning spots that are separated by a distance set by D, the separation of the centers of neighboring fibers. This distance D is a factor limiting the resolution of the imaging.

Some embodiments reduce the separation of scanning spots relative to the fixed-fiber systems by the bundle actuator 116 adjusting the configuration of the fiber bundle 102. In some embodiments, the bundle actuator 116 can adjust the configuration of the fiber bundle 102 after a first scan by the scanning unit 106. In some embodiments, the bundle actuator 116 can shift or rotate at least a portion of the fiber bundle 102 to a second position or configuration, as shown in FIG. 2b. For example, the bundle actuator 116 can rotate the fiber bundle 102 clockwise by an angle to the second rotated position. The fiber bundle 102 can be rotated by a small angle and by a corresponding small distance less than a distance or separation between the cores, which can be between 0.1 micron and a few hundred microns, For example, the fiber bundle 102 can be rotated by a small angle between 0 degree and 90 degrees in FIG. 2b, in order to direct the imaging beam to scanning spots between the spots reached before the rotation. The scanning unit 106 then can scan the imaging beam across the proximal face 114 of the fiber bundle 102 for the second time. After the second scan, the fiber bundle 102 can be rotated clockwise again to a third position, as shown in FIG. 2c. The scanning unit 106 can then scan the imaging beam across the proximal ends of the four cores for the third time. In this embodiment, the cores of the fiber bundle 102 can be rotated around a central longitudinal axis of the fiber bundle 102. In an embodiment, a core positioned at a center of the fiber bundle 102 can be rotated without changing positions relative to the central longitudinal axis of the fiber bundle 102.

Accordingly, FIG. 2d shows that by choosing an ever smaller rotation angle, the fibers can be rotated into a sequence of positions to cover the gaps between the optical fibers in small steps. When the scanning unit 106 re-scans the proximal surface 114 of the fiber bundle 102 after each of these small angle rotations, a density of the scanning spots can be increased considerably, enabling a higher resolution imaging.

In some embodiments, an actuator controller 117 can control the bundle actuator 116, and thereby the actuation of the fiber bundle 102. The actuator controller 117 can execute the actuation in coordination or synchronization with the scanning operation of the scanning unit 106. For example, the actuation of the fiber bundle 102 can begin after a scanning operation and can finish before the start of a subsequent scanning operation.

The actuator controller 117 can be in communication with the scanning unit 106 to coordinate the actuation and scanning operation. The actuator controller 117 can be a part of the actuator 116, or it can be disposed near the scanning unit 106, or it can be disposed in a separate console, in communication with a controller of the scanning unit 106. The actuator controller 117 can be synchronized with the scanning unit 106 via an electrical or mechanical, or electro-mechanical coupling.

In some embodiments, a proximal portion of the fiber bundle 102 can move or rotate together with a distal portion of the fiber bundle 102. In some embodiments, the entire fiber bundle 102 can rotate together. The bundle actuator 116 can be configured to cause both the proximal and distal portions of the fiber bundle 102 to rotate, laterally translate, and/or longitudinally translate together. Thus, the fiber bundle 102 can be rotated or moved without being twisted, if desired.

Figure 3:
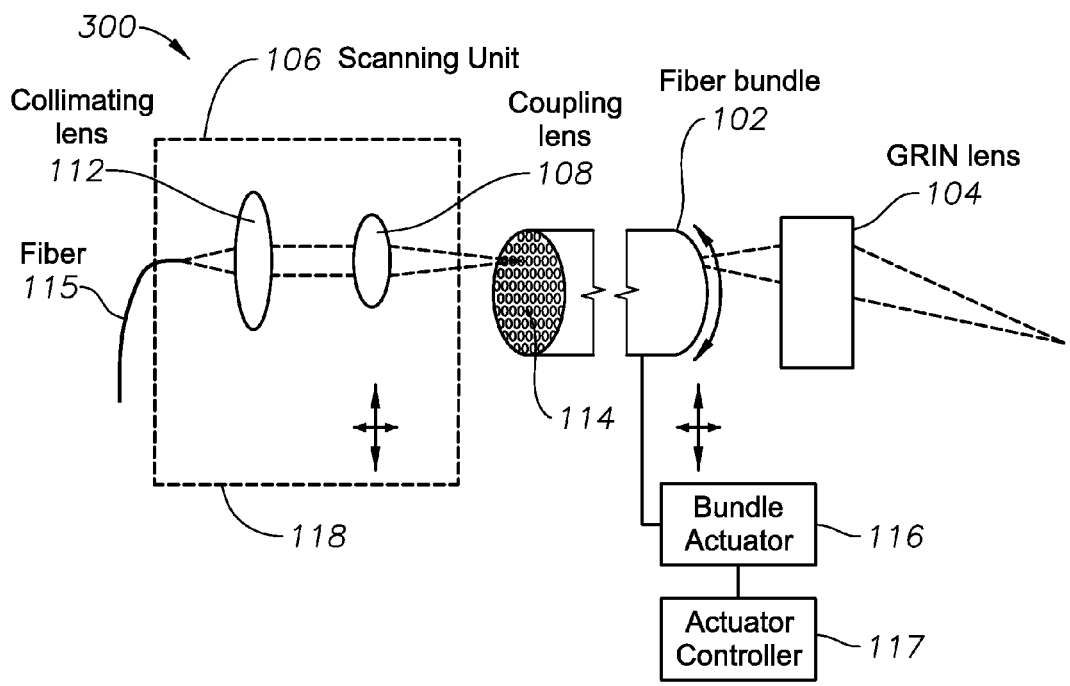
FIG. 3 illustrates an exemplary OCT imaging system.

FIG. 3 illustrates an OCT imaging apparatus 300. The OCT imaging apparatus 300 is similar in many respects to the OCT imaging apparatus 100 described above. For example, the scanning unit 106 can scan the imaging light across the proximal surface 114 of the fiber bundle 102. Further, the bundle actuator 116 can actuate the fiber bundle 102 to improve imaging resolution.

In addition, a movable stage 118 can be provided to perform the scanning action of the scanning unit 106. The movable stage 118 can move the scanning unit 106 to scan the imaging light across the proximal surface 114 of the fiber bundle 102. For example, the movable stage 118 can support the collimating lens 112 and the coupling lens 108. When the movable stage 118 moves, the beam of the imaging light can move to scan the proximal surface 114 of the fiber bundle 102. The scanning unit 106 can include multiple stages or actuators to move the scanning unit 106 in various directions.

Figure 4:
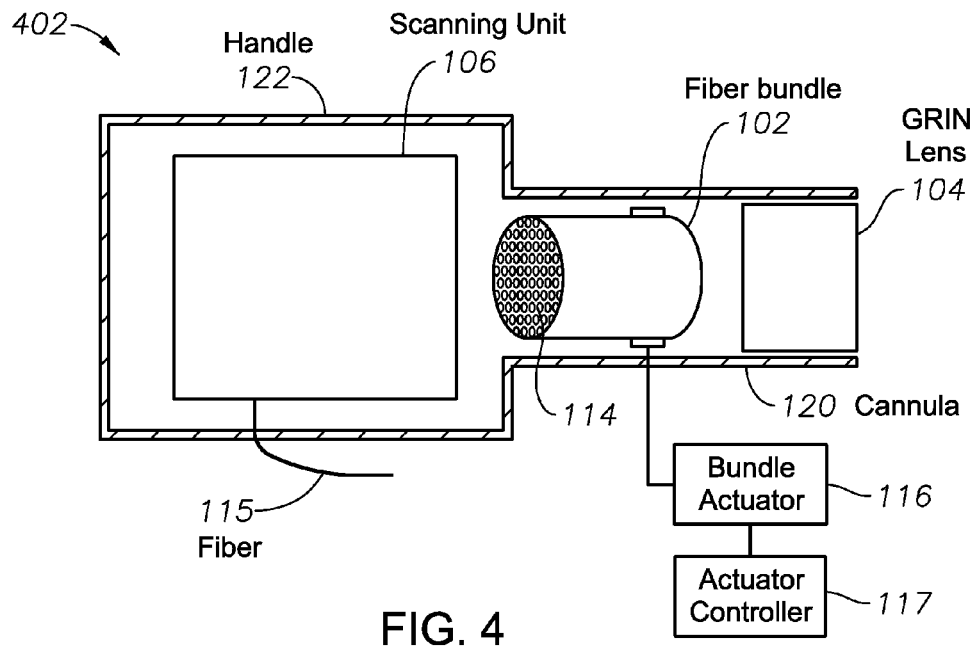
FIG. 4 illustrates a cross-sectional view of an imaging probe.

FIG. 4 illustrates a cross-sectional view of an imaging probe 402. In some designs, embodiments of the imaging probe 402 can accommodate or house the OCT imaging apparatus 100/300, or at least parts of it. The imaging probe 402 can include a handle 122, configured to be operated by a surgeon during operation, and a cannula 120, a distal end of which is configured to be inserted into a tissue, e.g., an eye. The scanning unit 106 can be positioned in the handle 122. The cannula 120 can be coupled to the handle 122, or protrude from the handle 122. The fiber bundle 102 can be positioned in the cannula 120, or at least parts of it in the cannula 120. The beam forming unit 104 can be positioned at a distal end of the cannula 120. The scanning unit 106 can scan the imaging light across the proximal surface 114 of the fiber bundle 102. The scanned imaging light, or beam, can be guided by the fiber bundle 102 to the beam forming unit 104. The beam forming unit 104 can direct, or redirect, the scanned imaging beam, and output the redirected scanned imaging beam toward the target tissue. The fiber bundle 102 can be actuated, as discussed above, to improve the imaging resolution.

Figure 5:
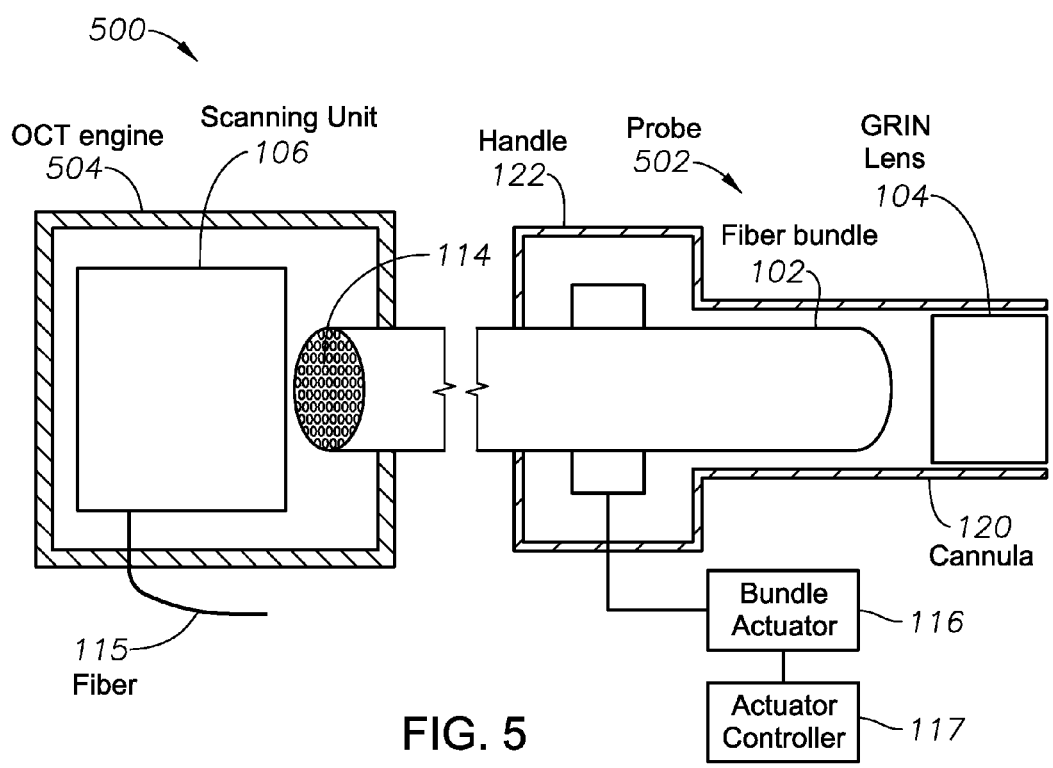
FIG. 5 illustrates a cross-sectional view of an imaging probe and an OCT engine.

FIG. 5 illustrates an OCT imaging apparatus 500. In a cross-sectional view, the OCT imaging apparatus 500 can include an imaging probe 502 and an OCT engine 504. The imaging probe 502 can be similar in many respects to the imaging probe 402 described above. For example, the imaging probe 502 can include a handle 122 configured to be operated by a surgeon during operation, and a cannula 120, a distal end of which is configured to be inserted into a tissue, e.g., an eye. Further, the cannula 120 can be coupled to the handle 122. The fiber bundle 102 can be positioned in the cannula 120. The beam forming unit 104 can be positioned at a distal end of the cannula 120.

In contrast to the imaging probe 402, in the presently shown design, the scanning unit 106 can be positioned in a separate OCT engine 504 spaced from the handle 122, such as in a separate console. The fiber bundle 102 can extend between the OCT engine 504 and the imaging probe 502. The OCT engine 504 can be configured to generate an OCT image from a returned scanned imaging light, returned from the target tissue.

For example, the OCT engine 504 can control the scanning unit 106 to scan the imaging light across the proximal surface 114 of the fiber bundle 102. The imaging light can be guided by the fiber bundle 102 from the OCT engine 504 to the imaging probe 502. Within the imaging probe 502, the fiber bundle 102 can guide the imaging light to the beam forming unit 104 to be output to the target tissue. The imaging light then can be reflected by the target tissue. The reflected imaging light can be captured back into the fiber bundle 102 via the beam forming unit 104. The reflected imaging light can be guided back to the OCT engine 504. The OCT engine 504 can analyze the reflected imaging light using OCT methods to generate an OCT image, including forming an interference with a reference beam. The generated OCT image can be displayed to the user, e.g., the surgeon, on a user interface display in communication with the OCT engine 504.

Figure 6A:
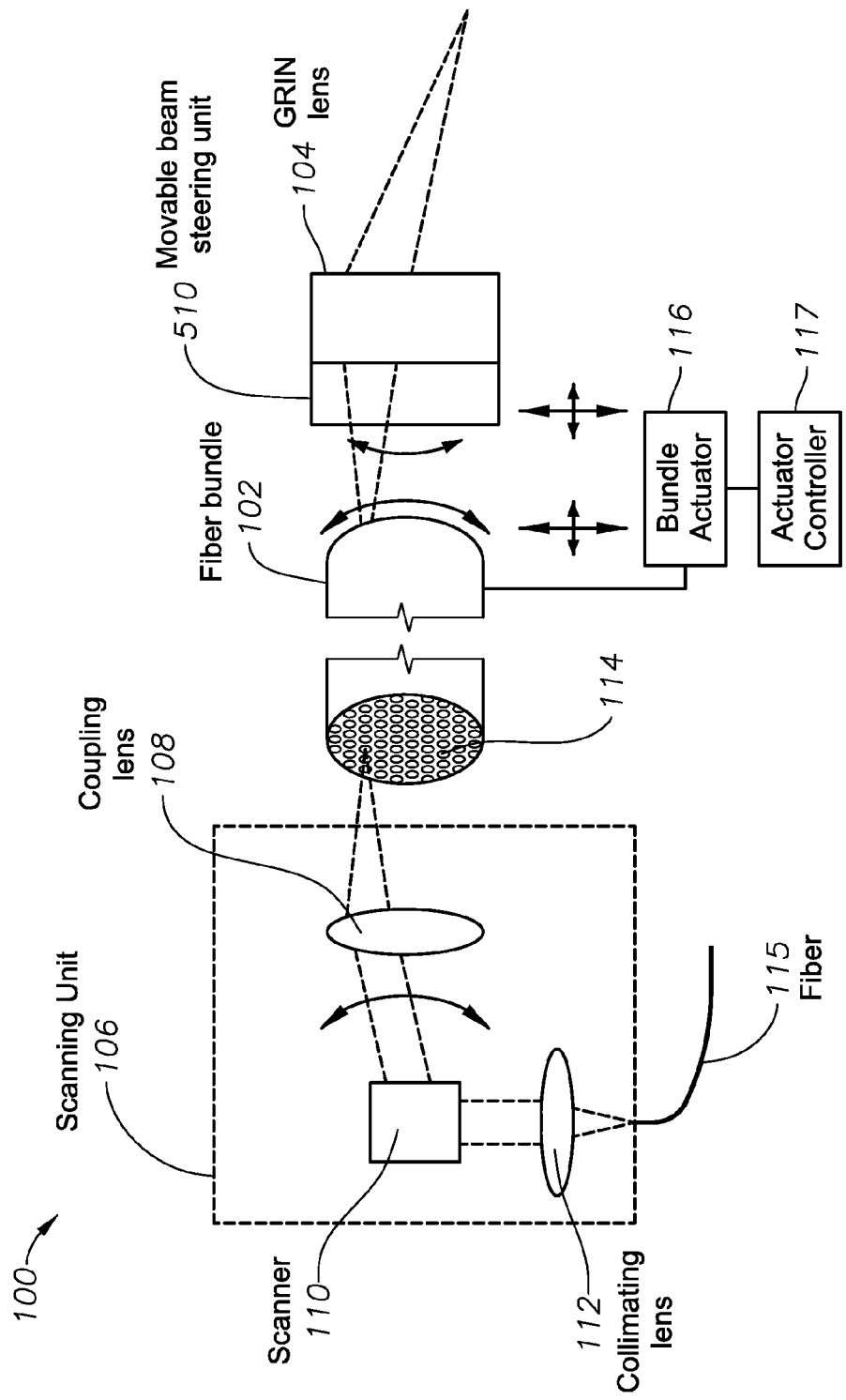
FIGS. 6*a*-*b* illustrate an OCT imaging system.
Figure 6B:
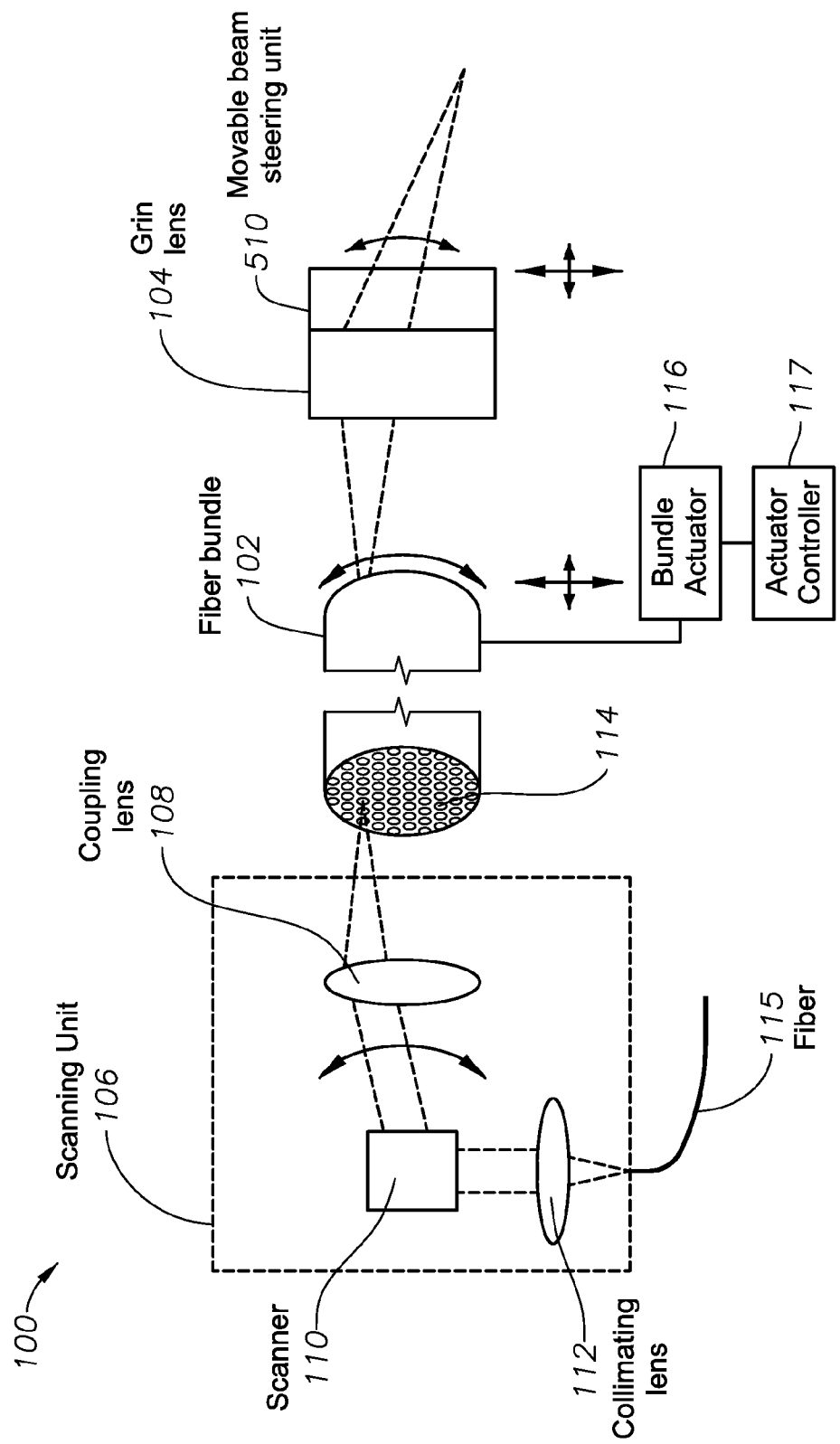

FIG. 6a illustrates that in some embodiments, the OCT imaging apparatus 100/300/500 can further include a movable beam steering unit 510 positioned at a distal end of the fiber bundle 102, but proximal to the beam forming unit 104, and configured to move to increase a density of scanning spots in a target tissue. FIG. 6b illustrates that in some embodiments, the OCT imaging apparatus 100/300/500 can further include a movable beam steering unit 510 positioned at a distal end of the beam forming unit 104 and configured to move to increase a density of scanning spots in a target tissue.

Figure 7:
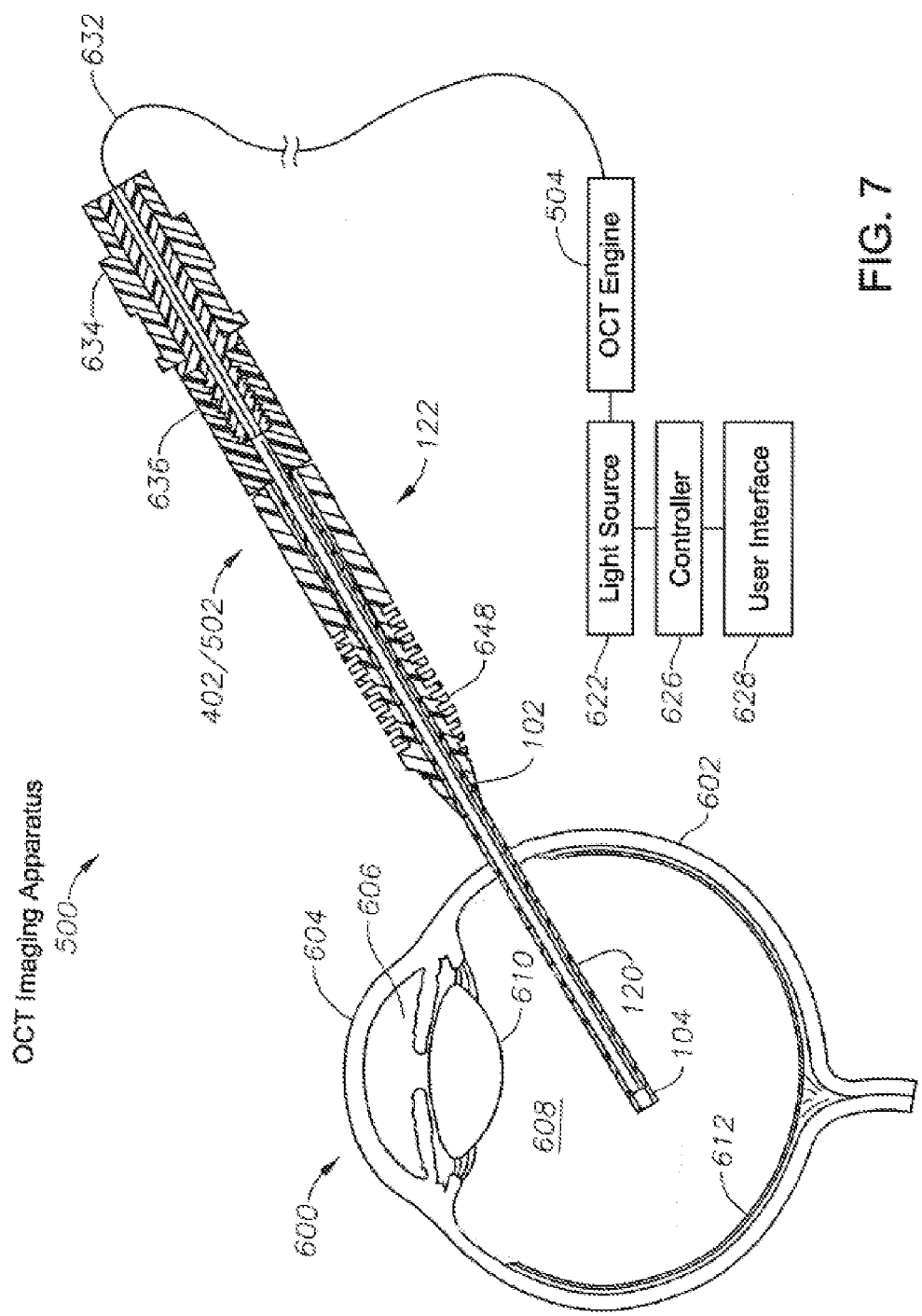
FIG. 7 illustrates an eye under treatment and an exemplary OCT imaging system.

FIG. 7 illustrates an eye under treatment by an OCT imaging apparatus 100/300/500. In particular, an eye 600 under treatment is shown. The eye 600 includes a sclera 602, a cornea 604, an anterior chamber 606, and a posterior chamber 608. A capsular bag 610 is illustrated in the posterior chamber 608. The eye 600 further includes a retina 612.

The OCT imaging apparatus 500 is also illustrated in FIG. 7. As discussed above, the OCT imaging apparatus 500 can be configured to image portions of the eye 600, such as the retina 612. The OCT imaging apparatus 500 can include an imaging light source 622, the optical coherence tomography (OCT) engine 504, a controller 626, a user interface 628, and the imaging probe 402/502. The light source 622 can be configured to provide imaging light that will be directed onto the target biological tissue by the imaging probe 502. The light source 622 can include super-luminescent diodes, ultra-short pulsed lasers, wavelength sweeping sources or supercontinuum lasers that provide relatively broad bandwidth light, such as between 700 nm and 1400 nm, between 900 nm and 1800 nm, or between 1000 nm and 1100 nm. Imaging light reflected from the target biological tissue and captured by the imaging probe 502 is utilized to generate images of the target biological tissue.

The OCT engine 504 is configured to split the imaging light received from the light source 622 into the imaging beam that is directed toward the target biological tissue by the imaging probe 502, and a reference beam that can be directed onto a reference mirror. The OCT engine 504 can be a spectral domain, swept-source, or a time domain system. The OCT engine 504 can be further configured to receive the imaging light reflected from the target biological tissue and captured by the imaging probe 502. The OCT engine 504 then can interfere the returned imaging beam and the reference beam, returned from the reference mirror to form an interference pattern. The interference pattern between the reflected imaging light and the reference beam can be utilized to generate an image of the target biological tissue. Accordingly, the OCT engine 504 can include a detector configured to detect the interference pattern. The detector can include photodiode detector, balanced detectors, Charge-Coupled Detectors (CCDs), pixels, or an array of any other type of sensor(s) that generate an electric signal based on detected light. Further, the detector can include a two-dimensional sensor array and a detector camera.

The controller 626 can include a processor and memory, which may include one or more executable programs for controlling operations of the light source 622, the user interface 628, the actuator controller 117 of the bundle actuator 116, and/or the imaging probe 502, and for executing and performing functions and processes to carry out an OCT imaging procedure. For example, the controller 626 can be configured to control the bundle actuator 116 in the imaging probe 502 to actuate a distal end of the fiber bundle 102 in sync with a scanning operation of the OCT imaging apparatus 500.

One or more of the light source 622, the OCT engine 504, the controller 626, and the user interface 628 can be implemented in a separate console communicatively coupled to one another, or within a common console. In some designs, parts of the OCT engine, such as its scanning unit 106 can be housed in the probe 402, as in FIG. 4. In other designs, the scanning unit can be house separately from the probe 502, such as in FIG. 5.

For example, in some implementations the light source 622, the OCT engine 504, and the controller 626 can be positioned within a console that is communicatively coupled to the user interface 628. The user interface 628 can be carried on or form part of the console. Further, the user interface 628, or at least part(s) thereof, can be separate from the console. The user interface 628 can include a display configured to present images to a user or a patient, and display tissue scanned by the imaging probe 502 during an OCT imaging procedure. The user interface 628 can also include input devices or systems, including by way of non-limiting example, a keyboard, a mouse, a joystick, a touchscreen, dials, and buttons, among other input devices.

In some designs, the imaging probe 402/502 can be in optical communication with the OCT engine 504. In that regard, the imaging probe 402/502 is configured to present light from the light source 622 that passes through OCT engine 504 onto the target biological tissue for the purpose of imaging the tissue. Further, the imaging probe 402/502 can be in electrical communication with the controller 626. In that regard, the controller 626 can control the bundle actuator 116 of the imaging probe 402/502 via electrical signals sent to the imaging probe 402/502 in order to cause the actuation system to scan the imaging beam across the target biological tissue. An optical cable 632 can connect the imaging probe 402/502 to the OCT engine 504 and/or the controller 626. In that regard, the cable 632 can include the fiber bundle 102, a fiber 115, electrical conductor(s), insulator(s), shield(s), and/or other features configured to facilitate optical and/or electrical communication between the imaging probe 402/502 and the OCT engine 504 and/or the controller 626. Further, it is understood that cable 632 can include multiple, separate cables. For example, in some instances an optical cable can connect the imaging probe 402/502 to the OCT engine 504, and a separate electrical cable can connect the imaging probe 402/502 to controller 626.

In the illustrated embodiment, the cable 632 can terminate in a connector 634 that is configured to facilitate removable coupling of the imaging probe 402/502 to the cable 632. The connector 634 can be configured to selectively engage with a connector 636 associated with the imaging probe 402/502 to facilitate mechanical, optical, and/or electrical coupling of the imaging probe 402/502 to the cable 632. For example, the fiber bundle 102 extending along the length of the imaging probe 402/502 can be optically coupled to the OCT engine 504 via the coupling of the connectors 634 and 636. In the illustrated embodiment, the connector 636 can be configured to threadingly engage with the connector 634. However, it is understood that any type of selective engagement feature(s) or connectors can be utilized to couple the imaging probe 402/502 to the cable 632, including without limitation press fit, luer lock, threads and combinations thereof. The selective engagement of the connector 636 with the connector 634 allows the entire probe 402/502 to be a disposable component configured for use in a single procedure, while the connector 634 and cable 632 can be reusable components that can be sterilized (e.g., using autoclave procedures) and used in multiple procedures. In the embodiments of FIG. 5, the cable 632 can be part of the imaging probe 402/502, and the connector coupling the imaging probe 402/502 and the cable 632 to the OCT engine 504 can be positioned in, next to, or close to the OCT engine 504.

The scanning unit 106 can be positioned in the disposable portion of the handle 122, or in a non-disposable and reusable portion of the handle 122, or in a separate portion of the OCT engine 504, again making it reusable.

The handle 122, sometimes also called the housing 122, can be sized and shaped for grasping by a hand of the user, such as the surgeon. To this end, the handle 122 can include a textured surface 648 (e.g., roughened, knurled, or include projections/recesses, tapers, other surface features, and/or combinations thereof) to enhance the user's grip on the handle 122. In operation, the user can control the position of the cannula 120, distally coupled to the housing/handle 122, by maneuvering the handle 122 such that the imaging light beam is directed towards the target biological tissue.

The cannula 120 can be sized and shaped for insertion into the eye 600 through the sclera 602 of the eye 600 to facilitate imaging of the retina 612. The cannula 120 can be integrally formed with the handle 122. Alternatively, the cannula 120 and the handle 122 can be separate components fixedly secured to one another. In that regard, the probe 402/502 can include one or more connectors to facilitate mechanical, optical, and/or electrical coupling of the cannula 120 and the handle 122. As a result, the cannula 120, or the cannula 120 and a portion of handle 122 can be a disposable component configured for use in a single procedure, while the handle 122 or remaining portions of the handle 122 are reusable components that can be sterilized (e.g., using autoclave procedures) and used in multiple procedures. In yet other embodiments, the entire handle 122 can be disposable. Finally, in some designs the entire probe 402/502 can be disposable. The beam forming unit 104, such as a lens, can be secured within the distal end of the cannula 120. The beam forming unit 104 can be configured to focus the imaging light onto the target biological tissue, such as the retina 612. The beam forming unit 104 can be a gradient index (GRIN) lens. Depending upon the embodiment, the gradient index may be spherical, axial, or radial. The beam forming unit 104 can also be a spherical lens. Other lens shapes may be used.

The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An optical imaging apparatus, comprising:
 a fiber bundle, comprising a set of optical fibers configured to guide an imaging light;
 a scanning unit, configured to scan the imaging light over a proximal surface of the fiber bundle using a scanning pattern;
 a beam forming unit, configured to receive the imaging light from the fiber bundle and to redirect the imaging light to a target region based on the scanning pattern; and
 a bundle actuator, configured to adjust a position of the set of optical fibers of the fiber bundle from a first position to at least one additional position different from the first position in cooperation with the scanning unit scanning the imaging light over the proximal surface of the fiber bundle to cause the redirected imaging light to cover areas associated with spacings between adjacent optical fibers of the fiber bundle when the fiber bundle is in the first position.

2. The optical imaging apparatus of claim 1, the scanning unit comprising at least one of:
 a rotatable mirror, a galvanometer, a resonant scanner, a polygon scanner, a MEMS scanner, and a movable stage.

3. The optical imaging apparatus of claim 1, wherein:
 the scanning unit comprises a movable stage; and
 the movable stage of the scanning unit and the proximal surface of the fiber bundle are coupled to move together.

4. The optical imaging apparatus of claim 1, the bundle actuator comprising:
 an actuator controller, coupled to the scanning unit and configured to control the bundle actuator to adjust the position of the set of optical fibers in relation to a scanning operation of the scanning unit.

5. The optical imaging apparatus of claim 1, wherein:
 the bundle actuator is configured to adjust a configuration of a distal portion of the set of optical fibers of the fiber bundle; and
the distal portion of the set of optical fibers is disposed in a cannula of an imaging probe.

6. The optical imaging apparatus of claim 1, wherein:
 the bundle actuator is configured to adjust a position of the set of optical fibers of the fiber bundle so that a distance between a center of a fiber in the first position and the center of the fiber in the second position is less than a distance between centers of adjacent optical fibers of the fiber bundle.

7. The optical imaging apparatus of claim 1, wherein:
 the bundle actuator is configured to rotate a distal portion of the set of optical fibers of the fiber bundle.

8. The optical imaging apparatus of claim 1, wherein:
 the bundle actuator is configured to twist a distal portion of the set of optical fibers of the fiber bundle.

9. The optical imaging apparatus of claim 1, wherein:
 the bundle actuator is configured to laterally translate a distal portion of the set of optical fibers of the fiber bundle.

10. The optical imaging apparatus of claim 1, wherein;
 the bundle actuator is configured to longitudinally translate at least one of a distal portion of the set of optical fibers of the fiber bundle and the beam forming unit.

11. The optical imaging apparatus of claim 10, wherein:
 the bundle actuator is part of a manual- or auto-focus sub-system, configured to longitudinally adjust at least one of the distal portion of the set of optical fibers of the fiber bundle and a position of the beam forming unit, to adjust a focal distance of the beam forming unit according to a working distance between an imaging target region and the beam forming unit in order to improve an imaging characteristics.

12. The optical imaging apparatus of claim 1, comprising:
 an imaging probe, comprising
 a handle, configured to house the scanning unit, and
 a cannula, coupled to the handle and configured to house at least a portion of the fiber bundle.

13. The optical imaging apparatus of claim 12, wherein:
 at least one of the handle and the imaging probe is disposable.

14. The optical imaging apparatus of claim 1, comprising:
 an imaging probe, configured to house at least a portion of the fiber bundle; and
 an optical coherence tomography (OCT) engine, configured
 to house the scanning unit, and
 to generate an OCT image from a returned scanned imaging light returned from an imaging target region.

15. The optical imaging apparatus of claim 14, wherein:
 the OCT engine is positioned in a console.

16. The optical imaging apparatus of claim 1, the scanning unit comprising:
 multiple stages and actuators.

17. The optical imaging apparatus of claim 1, the set of optical fibers of the fiber bundle comprising at least one of:
 a single mode fiber, a multi-mode fiber, a single-mode waveguide, a multi-mode waveguide, and a hollow tube.

18. The optical imaging apparatus of claim 1, the beam forming unit comprising at least one of:
 a lens, a GRIN lens, a ball lens, a diffractive element, an aspherical lens, and an objective lens.

19. The optical imaging apparatus of claim 1, comprising:
 a movable beam steering unit positioned distal to the distal end of the fiber bundle and configured to increase a density of scanning spots in an imaging target region.

20. The optical imaging apparatus of claim 19, wherein:
the movable beam steering unit is part of a manual- or auto-focus sub-system, configured to longitudinally adjust a position of an optical element of the beam forming unit according to a working distance between an imaging target region and the beam forming unit in order to improve an imaging characteristics.

21. A method of ophthalmic imaging, comprising:
scanning an imaging beam across a proximal end of a fiber bundle with a scanning unit;
directing the imaging beam by a beam forming unit to a target region of an eye; and
adjusting a configuration of a distal portion of the fiber bundle with a bundle actuator, wherein adjusting the configuration of the distal portion of the fiber bundle includes moving at least the distal portion of the fiber bundle from a first position to at least one additional position different from the first position in cooperation with the scanning of the imaging beam over the proximal end of the fiber bundle to cause the imaging beam to cover areas associated with spacings between adjacent optical fibers of the fiber bundle when the fiber bundle is in the first position.

22. The method of claim 21, wherein adjusting a configuration comprises:
adjusting the configuration of the distal portion of the fiber bundle with a bundle actuator so that a distance of a center of a fiber before and after the adjustment is less than a distance between centers of adjacent optical fibers of the fiber bundle.

* * * * *